United States Patent [19]

Imuta et al.

[11] Patent Number: 5,459,264
[45] Date of Patent: Oct. 17, 1995

[54] METHOD FOR REDUCING AN α β-UNSATURATED KETONE

[75] Inventors: Mitsuru Imuta, Neyagawa; Makoto Kobayashi, Takarazuka; Teruo Iizuka, Amagasaki, all of Japan

[73] Assignee: Shionogi Seiyaku Kabushiki Kaisha, Osaka, Japan

[21] Appl. No.: 169,614

[22] Filed: Dec. 17, 1993

[30] Foreign Application Priority Data

Dec. 21, 1992 [JP] Japan .................................. 4-340745

[51] Int. Cl.$^6$ .................. C07D 237/30; C07D 333/08; C07D 277/60
[52] U.S. Cl. .................... 544/237; 544/242; 544/257; 544/264; 544/283; 544/336; 544/353; 549/83; 549/305; 549/505; 546/102; 546/139; 546/164; 546/348; 548/127; 548/128; 548/134; 548/125; 548/131; 548/136; 548/146; 548/143; 548/215; 548/335.1; 548/373.1; 548/440; 548/449; 548/469; 548/560
[58] Field of Search ............................ 549/305, 83, 505; 544/237, 353, 264, 242; 546/102, 164, 348; 548/127, 136, 146, 215, 335.1, 440, 469, 560

[56] References Cited

FOREIGN PATENT DOCUMENTS 0543526  5/1993  European Pat. Off. ....... C07D 307/93

OTHER PUBLICATIONS

J. H. Brewster et al., "Hydrogenolyses with Chloroaluminum Hydrides. III. Allylic Alcohols", *J. Org. Chem.*, 29, pp. 116–121 (1964).

E. J. Corey et al., "New Reagents for Stereoselective Carbonyl Reduction. An Improved Synthetic Route to the Primary Prostaglandins", *J. Am. Chem. Soc.*, 93, pp. 1491–1493 (1971).

M. P. Doyle et al., "Silane Reductions in Acidic Media. VII. Aluminum Chloride Catalyzed Hydrogen–Halogen Exchange between Organosilanes and Alkyl Halides. An Efficient Hydrocarbon Synthesis", *J. Org. Chem.*, 41, pp. 1393–1396 (1976).

R. O. Hutchins et al., "Sodium Borohydride in Acetic Acid: A Convenient System for the Reductive Deoxygenation of Carbonyl Tosylhydrazones", *J. Org. Chem.*, 43, pp. 2299–2301 (1978).

D. N. Kursanove et al., "Applications of Ionic Hydrogenation to Organic Synthesis", Synthesis, 46, pp. 633–651 (1974).

*Primary Examiner*—C. Warren Ivy
*Assistant Examiner*—A. A. Owens
*Attorney, Agent, or Firm*—Fish & Neave; James F. Haley, Jr.; Kevin R. Hansbro

[57] ABSTRACT

A method for reducing an α,β-unsaturated ketone of the present invention includes the step of treating the α,β-unsaturated ketone with a silyl compound in the presence of a Lewis acid and alcohol to selectively reduce the carbonyl group of the α,β-unsaturated ketone. According to this method, a deoxy-compound can be obtained from the α,β-unsaturated ketone by selectively reducing the carbonyl group without reducing an α,β-unsaturated bond.

11 Claims, No Drawings

METHOD FOR REDUCING AN α β-UNSATURATED KETONE

BACKGROUND OF THE INVENTION

1. Field of the Invention

The present invention relates to a method for reducing an α,β-unsaturated ketone, and more particularly to a method for obtaining a deoxy-compound by selectively reducing the carbonyl group of the α,β-unsaturated ketone.

2. Description of the Related Art

Deoxygenation involving the reduction of an α,β-unsaturated ketone has been used for the synthesis of various medicines or medical materials. For example, it has been tried to obtain a deoxy-compound represented by the following Formula V, which is a useful starting material for preparing prostaglandins and derivatives thereof, by subjecting an α,β-unsaturated ketone represented by the following Formula III to a 1,2-reduction. When the 1,2-reduction is carried out according to conventional methods, the deoxy-compound V cannot be obtained by a single step but by complicated multiple steps as described below.

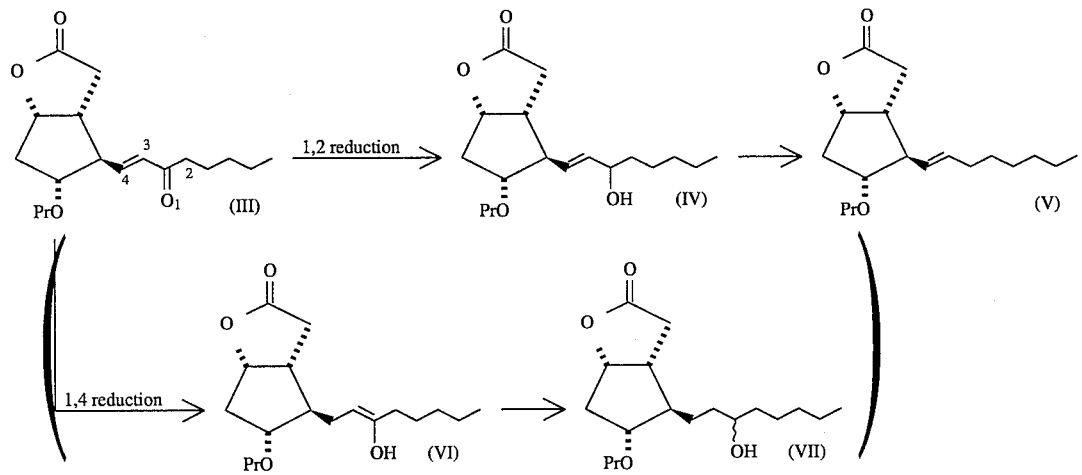

In the above reaction scheme, Pr is a hydroxy-protecting group.

Conventional methods for 1,2-reduction of the α,β-unsaturated ketone III are always accompanied by a 1,4-reduction as a side reaction. In the 1,4-reduction, the carbonyl group of the α,β-unsaturated ketone III is reduced to a hydroxyl group, and a double bond is migrated. As a result, a by-product VII which does not have a double bond is formed from the α,β-unsaturated ketone III via an intermediate VI.

Conventional methods for obtaining the deoxy-compound V by subjecting the α,β-unsaturated ketone III to the 1,2-reduction are known, in which a carbonyl group is reduced by two steps. According to one exemplary method, the carbonyl group of the α,β-unsaturated ketone III is reduced to obtain an allyl alcohol compound IV, and then the allyl alcohol compound IV is dehydroxylated to the deoxy-compound V. Another exemplary method is described in Journal of Organic Chemistry, Vol. 43, p. 2299 (1978). According to this method, the α,β-unsaturated ketone III is converted to the corresponding hydrazone, and thereafter, the hydrazone is reduced to obtain the deoxy-compound V. These methods have the following problems:

In the former method, when the α,β-unsaturated ketone III is reduced, the 1,4-reduction is simultaneously effected as described above. This causes the generation of the above-mentioned by-product VII, etc. together with the allyl alcohol compound IV. For this reason, a complicated step for separating the allyl alcohol compound IV from the by-product VII, etc. is required, resulting in poor productivity. In the latter method, the reduction of hydrazone causes the migration of the double bond. Thus, it is not possible to reduce only a carbonyl group.

Alternatively, a method for reducing a carbonyl group has been reported in Synthesis, p. 639 (1974), in which the α,β-unsaturated ketone is allowed to react with a silyl compound, using trifluoroacetic acid as an acid catalyst. According to this method, a great amount of by-product is generated by the 1,4-reduction; therefore, a deoxy-compound generated by the 1,2-reduction cannot be selectively obtained.

SUMMARY OF THE INVENTION

The method for reducing an α,β-unsaturated ketone of the present invention, comprises: the step of treating the α,β-unsaturated ketone with a silyl compound in the presence of a Lewis acid and alcohol to selectively reduce the carbonyl group of the α,β-unsaturated ketone.

In one embodiment of the present invention, the α,β-unsaturated ketone is a compound represented by the following Formula I:

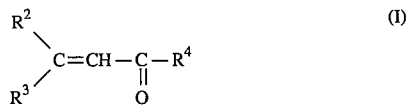

wherein $R^2$, $R^3$, and $R^4$ are independently selected from the group consisting of hydrogen, lower alkyl, lower alkenyl, cycloalkyl, cycloalkyl lower alkyl, lower alkoxy, amino, mono-(lower alkyl) amino, di-(lower alkyl) amino, carboxy, aryl, a heterocyclic group, aralkyl, aryloxy, aralkyloxy, alkanoyl, aroyloxy, alkylthio, alkoxycarbonyl, aryloxycarbonyl, aralkyloxycarbonyl, hydroxycarbamoyl, carbazoyl, carbamoyloxy, and derivatives thereof with a substituent.

In another embodiment of the present invention, the α,β-unsaturated ketone is a compound represented by the above-mentioned Formula I, wherein $R^2$ is a cycloalkyl or heterocyclic group, $R^3$ is hydrogen, and $R^4$ is lower alkyl.

In another embodiment of the present invention, the α,β-unsaturated ketone is a compound represented by the above-mentioned Formula I, wherein $R^2$ is a group selected from those represented by the following formulae:

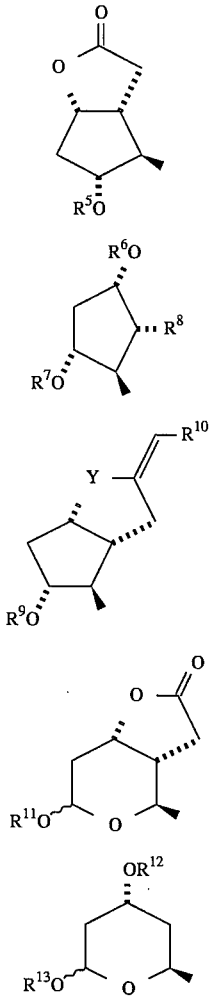

wherein Y is $CH_2$, oxygen, sulfur, or $SO_2$; $R^5$, $R^6$, $R^7$, $R^9$, $R^{11}$, $R^{12}$, and $R^{13}$ are independently hydrogen or a hydroxy-protecting group; $R^8$ is represented by the formula:

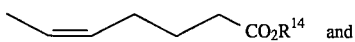

$R^{10}$ is represented by the formula:

where $R^{14}$ and $R^{15}$ are independently hydrogen or lower alkyl, $R^3$ is hydrogen, and $R^4$ is lower alkyl.

In another embodiment of the present invention, the α,β-unsaturated ketone is a compound represented by the following Formula IX:

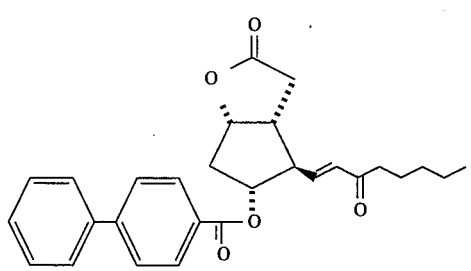

In another embodiment of the present invention, the alcohol is an alkanol having 1 to 8 carbon atoms.

In another embodiment of the present invention, the alcohol is isobutanol.

In another embodiment of the present invention, the silyl compound is $R^1{}_n SiH_{4-n}$, and n is 2 or 3 and $R^1$ is alkyl having 1 to 8 carbon atoms or halogen.

In another embodiment of the present invention, the silyl compound is triethylsilane.

In another embodiment of the present invention, the Lewis acid is $AlCl_3$.

Thus, the invention described herein makes possible the advantages of (1) providing a method for effectively obtaining a deoxy-compound from an α,β-unsaturated ketone by selectively reducing the carbonyl group without reduction of an α,β-unsaturated bond; (2) providing a method for obtaining a deoxy-compound from an α,β-unsaturated ketone by selectively reducing a carbonyl group without migration of a double bond in the α,β-unsaturated ketone, without causing the allyl rearrangement, and without affecting a functional group contained in a molecule of the α,β-unsaturated ketone, such as an ester group, an ether group, and a lactone ring; (3) providing a method for reducing an α,β-unsaturated ketone with high yield, in which the carbonyl group of the α,β-unsaturated ketone is reduced to obtain a deoxy-compound in a single batch, shortening the time required for the synthesis of the deoxy-compound; and (4) providing a method for reducing an α,β-unsaturated ketone which can be generally used for the reduction of the α,β-unsaturated ketone and which is particularly useful for the synthesis of prosraglandins.

These and other advantages of the present invention will become apparent to those skilled in the art upon reading and understanding the following detailed description.

DESCRIPTION OF THE PREFERRED EMBODIMENTS

The method for reducing an α,β-unsaturated ketone of the present invention includes the step of treating the α,β-unsaturated ketone with a silyl compound in the presence of a Lewis acid and alcohol to selectively reduce the carbonyl group of the α,β-unsaturated ketone, thereby obtaining a deoxy-compound.

An example of the α,β-unsaturated ketone to be reduced according to the present invention includes a compound represented by the following Formula I:

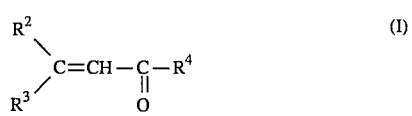

wherein $R^2$, $R^3$, and $R^4$ are independently selected from the group consisting of hydrogen, lower alkyl, lower alkenyl, cycloalkyl, cycloalkyl lower alkyl, lower alkoxy, amino, mono-(lower alkyl) amino, di-(lower alkyl) amino, carboxy, aryl, a heterocyclic group, aralkyl, aryloxy, aralkyloxy, alkanoyl, aroyloxy, alkylthio, alkoxycarbonyl, aryloxycarbonyl, aralkyloxycarbonyl, hydroxycarbamoyl, carbazoyl, carbamoyloxy, and derivatives thereof with a substituent.

Examples of the lower alkyl include straight-chain or branched-chain alkyl groups having 1 to 8 carbon atoms, such as methyl, ethyl, n-propyl, isopropyl, n-butyl, isobutyl, s-butyl, t-butyl, n-pentyl, isopentyl, neopentyl, s-pentyl, t-pentyl, n-hexyl, isohexyl, neohexyl, s-hexyl, t-hexyl, and the like. These groups can further have a substituent such as hydroxy, amino, carboxy, etc.

Examples of the lower alkenyl include straight-chain or branched-chain alkenyl groups having 2 to 8 carbon atoms, such as ethenyl, propenyl, butenyl, pentenyl, hexenyl, heptenyl, octenyl, propadienyl, butadienyl, pentadienyl, hexadienyl, heptadienyl, octadienyl, and the like. These groups can further have a substituent such as hydroxy, amino, carboxy, etc.

Examples of the cycloalkyl include cycloalkyl groups having 3 to 7 carbon atoms, such as cyclopropyl, cyclobutyl, cyclopentyl, cyclohexyl, cycloheptyl, and the like. These groups can be substituted by at least one substituent. Examples of the substituent include hydroxy, acetyloxy, and the like. The cycloalkyl can be condensed with a lactone ring.

The cycloalkyl lower alkyl refers to a group obtained by substituting the above-mentioned lower alkyl by the above-mentioned cycloalkyl. Examples of the cycloalkyl lower alkyl include cyclopropylmethyl, cyclobutylethyl, cyclohexyl-n-propyl, and the like.

Examples of the lower alkoxy include straight-chain or branched-chain alkyloxy groups having 1 to 6 carbon atoms, such as methoxy, ethoxy, n-propoxy, isopropoxy, n-butoxy, isobutoxy, s-butoxy, t-butoxy, n-pentyloxy, isopentyloxy, neopentyloxy, s-pentyloxy, t-pentyloxy, n-hexyloxy, isohexyloxy, neohexyloxy, s-hexyloxy, t-hexyloxy, and the like. These groups can further have a substituent such as hydroxy, amino, carboxy, etc.

The mono-(lower alkyl) amino refers to an amino group with one hydrogen atom thereof substituted by one of the above-mentioned lower alkyl groups. Examples of the mono-(lower alkyl) amino include methylamino, ethylamino, n-propylamino, isopropylamino, n-butylamino, isobutylamino, s-butylamino, t-butylamino, n-pentylamino, isopentylamino, n-hexylamino, isohexylamino, and the like.

The di-(lower alkyl) amino refers to an amino group with two hydrogen atoms thereof substituted by any different or identical two of the above-mentioned lower alkyl groups. Examples of the di-(lower alkyl) amino include dimethylamino, diethylamino, methylethylamino, methylpropylamino, ethylpropylamino, dipropylamino, dibutylamino, dipentylamino, dihexylamino, pentylhexylamino, and the like.

Any different or identical two groups which substitute for two hydrogen atoms in an amino group can form a ring together with a nitrogen atom in the amino group. The ring can further have nitrogen, oxygen, and/or sulfur. Examples of such a cyclic group include polymethylene cyclic imino (e.g., pyrrolidino, piperidino, piperazino, etc.), N-substituted piperazino, morpholino, thiomorpholino, homopiperazino, N-substituted homopiperazino, and the like.

Examples of the aryl include phenyl, α-naphthyl, β-naphthyl, and the like. These groups can further have a substituent such as hydroxy, amino, carboxy, etc.

Examples of the heterocyclic group include an aromatic heterocyclic group and a saturated heterocyclic group.

Examples of the aromatic heterocyclic groups include aromatic heterocyclic groups having 5 to 6 members, each having at least one oxygen atom, sulfur atom, or nitrogen atom in its ring and capable of being condensed with another aromatic ring. Specific examples of the aromatic heterocyclic group include pyrrolyl, indolyl, carbazolyl, imidazolyl, pyrazolyl, benzimidazolyl, indazolyl, indolizinyl, pyridyl, quinolyl, isoquinolyl, acridinyl, phenanthridinyl, pyridazinyl, pyrimidinyl, pyrazinyl, cinnolinyl, phthalazinyl, quinazolinyl, naphthyridinyl, quinoxalinyl, phenazinyl, 1,3,5-triazinyl, 1,2,4-triazinyl, 1,2,3-triazinyl, purinyl, pteridinyl, isoxazolyl, benzisoxazolyl, oxazolyl, benzoxazolyl, 1,2,3-oxadiazolyl, 1,2,4-oxadiazolyl, 1,2,5-oxadiazolyl, 1,3,4-oxadiazolyl, benzoxadiazolyl, isothiazolyl, benzisothiazolyl, thiazolyl, benzthiazolyl, 1,2,3-thiadiazolyl, 1,2,4-thiadiazolyl, 1,2,5-thiadiazolyl, 1,3,4-thiadiazolyl, benzthiadiazolyl, furyl, benzofuranyl, thienyl, benzothienyl, and the like. These groups can further have a substituent such as hydroxy, amino, carboxy, etc.

Examples of the saturated heterocyclic group include a saturated heterocyclic group having 3 to 8 members, each having at least one oxygen atom, sulfur atom, or nitrogen atom in its ring. Specific examples of the heterocyclic group include azetidinyl, pyrrolidinyl, piperidinyl, morpholinyl, thiomorpholinyl, piperazinyl, oxiranyl, thietanyl, and the like. These groups can further have a substituent such as hydroxy, amino, carboxy, etc.

The aralkyl refers to a group obtained by substituting a hydrogen atom of the above-mentioned lower alkyl by the above-mentioned aryl. Examples of the aralkyl include benzyl, phenethyl, phenylpropyl, α-naphthylmethyl, β-naphthylmethyl, and the like.

Examples of the aryloxy include phenyloxy, α-naphthyloxy, β-naphthyloxy, and the like. These groups can further have a substituent such as hydroxy, amino, carboxy, etc.

Examples of the aralkyloxy include phenethyloxy, phenylpropyloxy, and the like.

The alkanoyl refers to a group in which the above-mentioned lower alkyl is bound to carbonyl. Examples of the alkanoyl include acetyl, propionyl, butyryl, etc.

Examples of the aroyloxy include benzoyloxy, naphthoyloxy, and the like. These groups can further have a substituent such as hydroxy, amino, carboxy, etc.

The alkylthio refers to a group in which the above-mentioned lower alkyl is bound to a sulfur atom. Examples of the alkylthio include methylthio, ethylthio, propylthio, butylthio, hexylthio, and the like.

The alkoxycarbonyl refers to a group in which the above-mentioned lower alkoxy is bound to carbonyl. Examples of the alkoxycarbonyl include methoxycarbonyl, ethoxycarbonyl, propoxycarbonyl, and the like.

Examples of the aryloxycarbonyl include phenyloxycarbonyl, α-naphthyloxycarbonyl, β-naphthyloxycarbonyl, and the like. These groups can further have a substituent group such as hydroxy, amino, carboxy, etc.

Examples of the aralkyloxycarbonyl include phenethyloxycarbonyl, phenylpropyloxycarbonyl, and the like.

Specific examples of the α,β-unsaturated ketone include compounds represented by Formula I, wherein $R^2$ is a cycloalkyl or heterocyclic group, $R^3$ is hydrogen, and $R^4$ is lower alkyl.

Preferably, $R^2$ in the above-mentioned cycloalkyl group or heterocyclic group is a group selected from those represented by the following formulae:

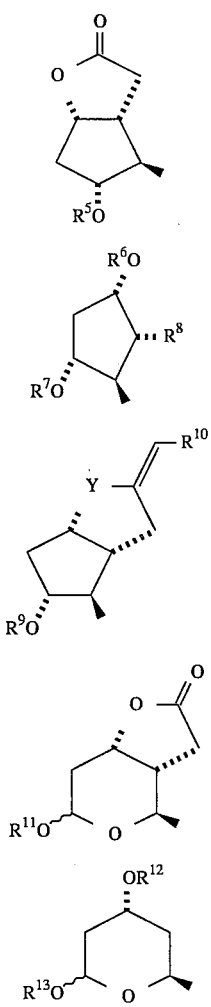

wherein Y is $CH_2$, oxygen, sulfur, or $SO_2$; $R^5$, $R^6$, $R^7$, $R^9$, $R^{11}$, $R^{12}$, and $R^{13}$ are independently hydrogen or a hydroxy-protecting group; $R^8$ is represented by the formula:

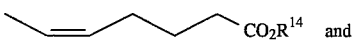

and $R^{10}$ is represented by the formula:

where $R^{14}$ and $R^{15}$ are independently hydrogen or lower alkyl.

When the α,β-unsaturated ketone has a substituent which is likely to be affected by reduction, such as hydroxy, amino, carboxy, etc., the substituent is preferably protected by any known protecting group.

For protecting a hydroxyl group, among the groups which are generally used as a hydroxy-protecting group, which are not released in the course of the process of the present invention can be used. Examples of such protecting groups include various protecting groups described in Protective groups in organic synthesis. T. W. Greene, John Wiley & Sons, Inc., New York, p. 10, 1991. Specific examples thereof include alkyl(thio)ether type protecting groups such as methyl, methoxymethyl, methylthiomethyl, 2-methoxy-ethoxymethyl, 1-ethoxyethyl, and the like; silyl ether type protecting groups such as triethylsilyl, t-butyldimethylsilyl, t-butyldiphenylsilyl, and the like; acyl type protecting groups such as acetyl, benzoyl, p-methylbenzoyl, o-methoxybenzoyl, p-phenylbenzoyl, and the like; and aralkyl type protecting groups such as benzyl, p-methoxybenzyl, and the like.

Preferably, the α,β-unsaturated ketone is a compound represented by the following Formula IX

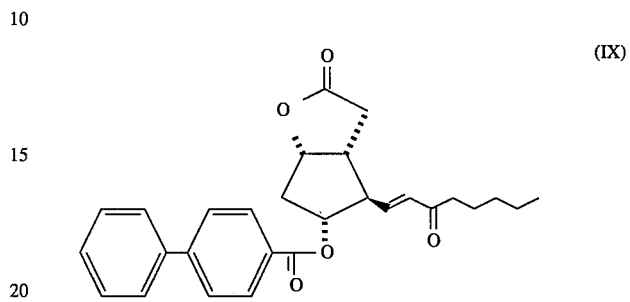

According to the method of the present invention, a carbonyl group of the α,β-unsaturated ketone represented by the following Formula III is reduced in a single batch to obtain the deoxy-compound V.

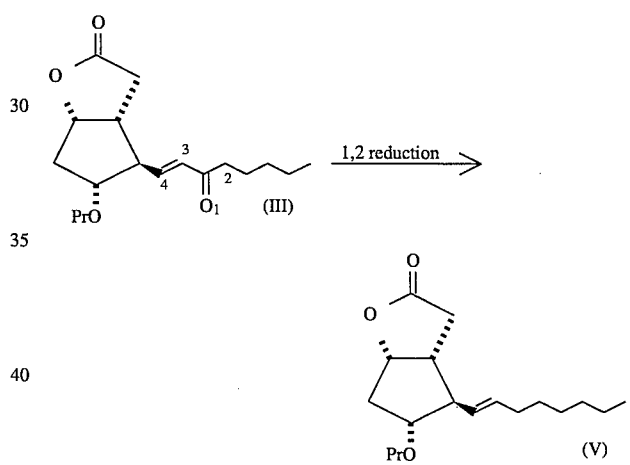

wherein Pr is a hydroxy-protecting group.

In the case of the α,β-unsaturated ketone represented by Formula III, p-phenylbenzoyl, for example, is preferably used as a protecting group because of good crystallinity of both the starting material and the resulting product.

Examples of alcohol used for the method of the present invention include an alkanol having 1 to 8 carbon atoms. An alkyl group of the alcohol may be a straight-chain or a branched-chain. Specific examples of such alcohol include methanol, ethanol, n-propanol, isopropanol, n-butanol, isobutanol, isopentanol, and the like. In particular, isobutanol is preferably used.

It was confirmed that if the amount of alcohol is increased, the side reactions (in particular, 1,4-reduction) are suppressed and the selectivity of the 1,2-reduction is increased. The minimum amount of alcohol to be used need not be fixed; however, the addition of at least 0.1 equivalent of alcohol per equivalent of the α,β-unsaturated ketone is considered sufficient to increase the selectivity of the 1,2-reduction. The maximum amount of alcohol need not be fixed, either; however, the addition of more than 10 equivalents of alcohol per equivalent of the α,β-unsaturated ketone is considered sufficient to cause another side reaction, thereby decreasing the yield of the deoxy-compound, although the 1,4-reduction is suppressed. Thus, in order to achieve the present invention, the alcohol to be used is preferably in an amount of about 0.1 to 10 equivalents, more preferably about 1 to 4 equivalents, and the most preferably 2 to 3 equivalents per equivalent of the α,β-unsaturated ketone.

Examples of the silyl compound used for the method of the present invention include compounds represented by the formula: $R^1_n SiH_{4-n}$, wherein n is 2 or 3 and $R^1$ is alkyl having 1 to 8 carbon atoms or halogen. Specific examples of the silyl compound include trimethylsilane, triethylsilane, tripropylsilane, tributylsilane, diethylsilane, trichlorosilane, and the like. In particular, triethylsilane is preferably used.

The silyl compound is used in an amount of 2 to 3 equivalents, preferably 2 equivalents per equivalent of the α,β-unsaturated ketone.

Examples of the Lewis acid used for the method of the present invention include $AlCl_3$, $CeCl_3$, $TiCl_4$, and the like. In particular, $AlCl_3$ is preferably used.

The Lewis acid is used in an amount of 1 to 6 equivalents, preferably 4 to 6 equivalents per equivalent of the α,β-unsaturated ketone. Equivalents of Lewis acid per equivalent of ketone are calculated by dividing the moles of Lewis acid used by the moles of ketone used.

The reduction according to the method of the present invention is carried out, preferably, in a solvent. The solvent is appropriately selected based on the kind of α,β-unsaturated ketone. Examples of the solvent to be used include halogenated hydrocarbons such as methylene chloride, dichloroethane, chloroform, and the like; acetic esters such as ethyl acetate and the like; aromatic hydrocarbons such as benzene, toluene, xylene, and the like; ethers such as tetrahydrofuran, diethyl ether, dioxane, ethylene glycol dimethyl ether, and the like; aliphatic hydrocarbons such as hexane, heptane, cyclohexane, pentane, and the like; acetonitrile; dimethylformamide; dimethyl sulfoxide, etc. In particular, the halogenated hydrocarbons are preferably used. The solvent can be used alone or in combination.

The reduction is carried out at a temperature in the range of −35° C. to 0° C., preferably in the range of −35° C. to −30° C. When the reduction is carried out at a temperature in the range of −35° C. to −30° C., a deoxy-compound can be obtained with particularly high yield and good selectivity.

The deoxy-compound thus obtained (e.g., the compound represented by Formula V) is preferably used for starting materials for preparing a medicine such as those for the synthesis of prostaglandins.

Hereinafter, the present invention will be described by way of illustrative examples.

EXAMPLE 1

Synthesis of [3aR-[3aα, 4α(1E), 5β, 6aα]]-hexahydro-4-(3-oxo-1-octenyl)-2-oxo-2H-cyclopenta[b]furan-5-yl (1,1'-biphenyl)-4-carboxylate The subject compound is represented by the following Formula VIII, and the compound is hereinafter referred to as deoxylactone.

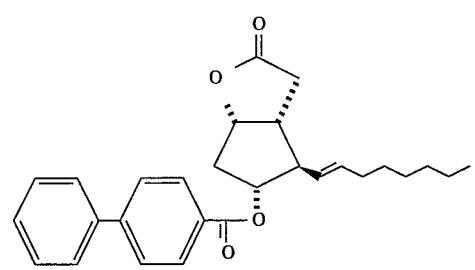

First, 560 ml (2.15 equivalents) of triethylsilane was added to 10 ml of methylene chloride. The mixture thus obtained was cooled to −35° C. in an atmosphere of nitrogen, and then, 1.79 g (6 equivalents) of anhydrous $AlCl_3$ and 0.5 g (3 equivalents) of isobutanol were successively added to the mixture with stirring to obtain a mixed solution. Thereafter, 5 ml of methylene chloride solution in which 1 g (1 equivalent) of α,β-unsaturated ketone (hereinafter, referred to as enone) represented by the following Formula IX was dropped to the mixed solution thus obtained, and allowed to react with stirring at −30° C. for 2 hours. After the reaction, 10 ml of water was added to the reaction solution and a methylene chloride layer was separated. The methylene chloride layer was washed with 10 ml of water and then concentrated under reduced pressure.

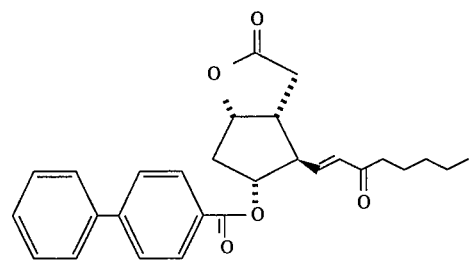

The HPLC analysis revealed that the reaction product obtained as a residue by the concentration under reduced pressure contains 87% deoxylactone which is a desired product and 6% by-product having no double bond generated by the 1,4-reduction. The by-product is represented by the following Formula X:

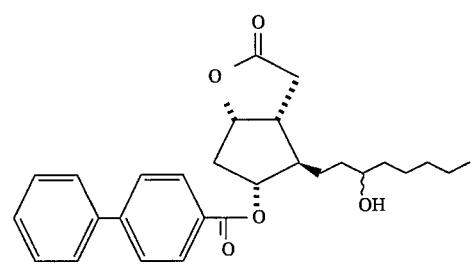

The reaction product thus obtained was dissolved in 3 ml of ethanol (95%) at room temperature. Then, the ethanol solution was ice-cooled with stirring for 1 hour, resulting in the formation of a crystalline precipitation. The precipitated crystal was collected by filtration. The crystal was washed with 3 ml of cold ethanol (95%) and dried to obtain 775 mg of deoxylactone VIII (yield: 80%) as white crystalline powder.

Separately, 10 ml of methylene chloride was added to the filtrate. The mixed solution was washed with water, and evaporated under reduced pressure. The residue thus obtained was subjected to silica gel chromatography, and eluted with ethyl acetate-hexane (1:1) to obtain 38 mg of by-product X (yield: 3.8%) as a colorless oil.

The melting point of the white crystalline powder was measured. The white crystalline powder and the colorless oil were analyzed by infrared absorption spectroscopy (IR) and nuclear magnetic resonance spectroscopy (NMR). These results are shown below.

Deoxylactone VIII (White Crystalline Powder)
  Melting point: 73° to 74° C.
  $IR(CHCl_3)$: 1765, 1710, 1605, 972 $cm^{-1}$
  $NMR(CDCl_3)$: δ0.85 (t, J=6 Hz, 3H), 1.18 to 1.70 (m, 8H), 1.90 to 3.00 (m, 8H), 5.02 to 5.38 (m, 3H), 5.52 to 1.70 (m, 1H), 7.38 to 7.70 (m, 7H), 8.10 (m, 2H).

By-product X (Colorless Oil)
  IR(neat): 3500, 1765, 1710, 1605 $cm^{-1}$
  $NMR(CDCl_3)$: δ0.87 (t, J=6 Hz, 3H), 1.20 to 1.90 (m, 13H), 2.21 to 3.11 (m, 6H), 3.60 (m, 1H), 5.12 (m, 1H), 5.30 (m, 1H), 7.35 to 7.70 (m, 7H), 8.05 (m, 2H).

EXAMPLE 2

The reaction was carried out by the same process as in Example 1, with the following alteration:

Triethylsilane in methylene chloride was cooled to −5° C. in an atmosphere of nitrogen. Then, anhydrous $AlCl_3$ and isobutanol were successively added to the solution. The mixed solution thus obtained and a methylene chloride solution of the enone were allowed to react with stirring at 0° C. for 1 hour.

The HPLC analysis revealed that the reaction product contains 75% deoxylactone VIII and 14% by-product X.

From the reaction product thus obtained, 668 mg of the deoxylactone (yield: 69%) was obtained as white crystalline powder in the same way as in Example 1. The deoxylactone was identified by means of the IR and NMR analysis with the use of the deoxylactone obtained in Example 1 as a standard.

EXAMPLE 3

The reaction was carried out by the same process as in Example 1, with the following alteration:

Triethylsilane in methylene chloride was ice-cooled in an atmosphere of nitrogen. Then, anhydrous $AlCl_3$ and isobutanol were successively added to the solution. The mixed solution thus obtained and a methylene chloride solution of the enone were allowed to react with stirring at room temperature for 30 minutes.

The HPLC analysis revealed that the reaction product contains 66% deoxylactone VIII and 26% by-product X.

From the reaction product thus obtained, 581 mg of the deoxylactone (yield: 60%) was obtained as white crystalline powder in the same way as in Example 1. The deoxylactone was identified by means of the IR and NMR analysis with the use of the deoxylactone obtained in Example 1 as a standard.

EXAMPLE 4

The reaction was carried out by the same process as in Example 1, except that 0.1 g of isobutanol (0.6 equivalent) was added.

The HPLC analysis was conducted in the same way as in Example 1. The results are shown in Table 1. The deoxylactone was identified by means of the IR and NMR analysis with the use of the deoxylactone obtained in Example 1 as a standard.

EXAMPLES 5 TO 9

The reaction was carried out by the same process as in Example 1, except that isobutanol was added in an amount shown in Table 1. The HPLC analysis was conducted in the same way as in Example 1. The results are shown in Table 1. The deoxylactone was identified by means of the IR and NMR analysis with the use of the deoxylactone obtained in Example 1 as a standard.

TABLE 1

| | Added amount of isobutanol | Reaction product | |
|---|---|---|---|
| | (g) (equivalents) | Deoxylactone VIII (%) | By-product X (%) |
| Example 4 | 0.1 (0.6) | 73 | 14 |
| Example 5 | 0.2 (1.2) | 84 | 8 |
| Example 6 | 0.4 (2.4) | 86 | 7 |
| Example 7 | 0.5 (3.0) | 87 | 6 |
| Example 8 | 0.6 (3.6) | 84 | 6 |
| Example 9 | 0.7 (4.2) | 78 | 4 |

COMPARATIVE EXAMPLE 1

The reaction was carried out by the same process as in Example 1, except that alcohol was not added in the process. The HPLC analysis was conducted in the same way as in Example 1, revealing that the reaction product contains 54% deoxylactone VIII and 26% by-product X. As is understood from this result, the yield of deoxylactone was low in the absence of alcohol.

EXAMPLE 10

The reaction was carried out in the same way as in Example 1, except that 0.33 g of $CeCl_3 \cdot 7H_2O$ (0.4 equivalents) was added as a Lewis acid in addition to $AlCl_3$.

The HPLC analysis revealed that the reaction product contains 75% deoxylactone VIII and 8% by-product X.

EXAMPLE 11

The reaction was carried out by the same process as in Example 1, with the following alteration:

Triethylsilane in methylene chloride was cooled to −5° C. in an atmosphere of nitrogen. Then, 0.25 g of anhydrous $TiCl_4$ (0.6 equivalents) and 0.5 g of isobutanol (3 equivalents) were successively added to the solution. The mixed solution thus obtained and a methylene chloride solution of the enone were allowed to react with stirring at 0° C. for 3 hours.

The HPLC analysis revealed that the reaction product contains 62% deoxylactone VIII and 4% by-product X.

EXAMPLES 12 TO 17

The reaction was carried out by the same process as in Example 1, except that alcohols shown in Table 2 were used respectively in an amount of 3 equivalents. Each composition of the reaction products is shown in Table 2. The results of Example 1 and Comparative Example 1 are also shown in Table 2 for reference.

TABLE 2

| | Alcohol | Reaction product Deoxylactone VIII (%) | By-product X (%) |
|---|---|---|---|
| Example 1 | isobutanol | 87 | 6 |
| Example 12 | methanol | 69 | 10 |
| Example 13 | ethanol | 82 | 6 |
| Example 14 | n-propanol | 87 | 5 |
| Example 15 | isopropanol | 86 | 5 |
| Example 16 | n-butanol | 87 | 6 |
| Example 17 | isopentanol | 82 | 9 |
| Comparative Example 1 | None | 54 | 26 |

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for reducing an α,β-unsaturated ketone comprising the step of treating the α,β-unsaturated ketone with a silyl compound in the presence of a Lewis acid and alcohol to selectively reduce the carbonyl group of the α,β-unsaturated ketone, wherein the α,β-unsaturated ketone is a compound represented by the following Formula I:

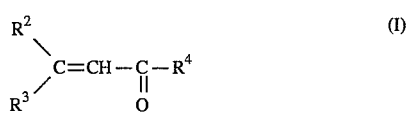

wherein $R^2$, $R^3$, and $R^4$ are independently selected from the group consisting of hydrogen, lower alkyl, cycloalkyl, cycloalkyl lower alkyl, a heterocyclic group, and derivatives thereof with a substituent.

2. A method for reducing an α,β-unsaturated ketone according to claim 1, wherein $R^2$ is a cycloalkyl, aromatic heterocyclic group, or saturated heterocyclic group, $R^3$ is hydrogen, and $R^4$ is a lower alkyl.

3. A method for reducing an α,β-unsaturated ketone according to claim 2, wherein $R^2$ is a group selected from those represented by the following formulae:

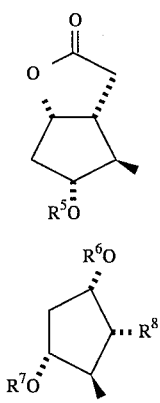

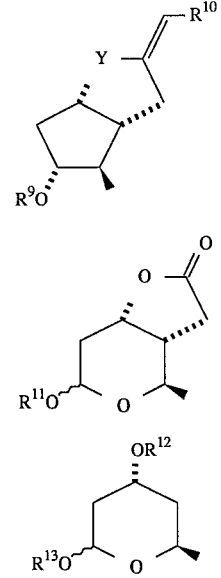

wherein Y is $CH_2$, oxygen, sulfur, or $SO_2$; $R^5$, $R^6$, $R^7$, $R^9$, $R^{11}$, $R^{12}$, and $R^{13}$ are independently hydrogen or a hydroxy-protecting group; $R^8$ is represented by the formula:

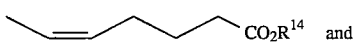

$R^{10}$ is represented by the formula:

where $R^{14}$ and $R^{15}$ are independently hydrogen or lower alkyl.

4. A method for reducing an α,β-unsaturated ketone according to claim 1, wherein the α,β-unsaturated ketone is a compound represented by the following Formula IX:

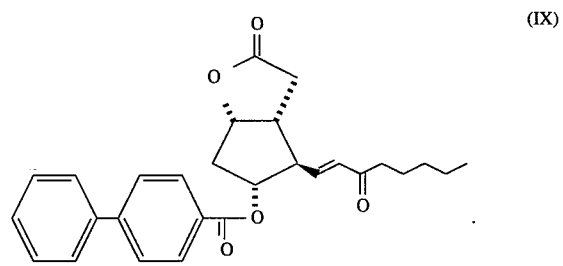

5. A method for reducing an α,β-unsaturated ketone according to claim 1 or 4, wherein the alcohol is an alkanol having 1 to 8 carbon atoms.

6. A method for reducing an α,β-unsaturated ketone according to claim 5, wherein the alcohol is isobutanol.

7. A method for reducing an α,β-unsaturated ketone according to claim 1 or 4, wherein the silyl compound is $R^1_n SiH_{4-n}$, and n is 2 or 3 and $R^1$ is alkyl having 1 to 8 carbon atoms or halogen.

8. A method for reducing an α,β-unsaturated ketone according to claim 7, wherein the silyl compound is triethylsilane.

9. A method for reducing an α,β-unsaturated ketone according to claim 1 or 4, wherein the Lewis acid is $AlCl_3$.

10. A method for reducing an α,β-unsaturated ketone according to claim 2, wherein $R^2$ is a group selected from the group consisting of pyrrolyl, indolyl, carbazolyl, imidazolyl, pyrazolyl, benzimidazolyl, indazolyl, indolizinyl, pyridyl, quinolyl, isoquinolyl, acridinyl, phenanthridinyl, pyridazinyl, pyrimidinyl, pyrazinyl, cinnolinyl, phthalazinyl, quinazolinyl, naphthyridinyl, quinoxalnyl, phenazinyl, 1,3,5-triazinyl, 1,2,4-triazinyl, 1,2,3-triazinyl, purinyl, pteridinyl, isoxazolyl, benzisoxazolyl, oxazolyl, benzoxazolyl, 1,2,3-oxadiazolyl, 1,2,4-oxadiazolyl, 1,2,5-oxadiazolyl, 1,3,4-oxadiazolyl, benzoxadiazolyl, isothiazolyl, benzisothiazolyl, thiazolyl, benzthiazolyl, 1,2,3-thiadiazolyl, 1,2,4-thiadiazolyl, 1,2,5-thiadiazolyl, 1,3,4-thiadiazolyl, benzthiadiazolyl, furyl, benzofuranyl, thienyl, and benzothienyl.

11. A method for reducing an α,β-unsaturated ketone according to claim 2, wherein $R^2$ is a group selected from the group consisting of azetidinyl, pyrrolidinyl, piperidinyl, morpholinyl, thiomorpholinyl, piperazinyl, oxiranyl, and thietanyl.

* * * * *